United States Patent
Haindl

[11] Patent Number: 5,931,867
[45] Date of Patent: Aug. 3, 1999

[54] RADIALLY EXPANDABLE SUPPORT DEVICE

[75] Inventor: Hans Haindl, Wennigsen, Germany

[73] Assignee: W.C. Heraeus GmbH, Hanau, Germany

[21] Appl. No.: 09/066,252

[22] Filed: Apr. 24, 1998

[30] Foreign Application Priority Data

Apr. 25, 1997 [DE] Germany .......................... 197 17 475

[51] Int. Cl.⁶ ....................................................... A61F 2/06
[52] U.S. Cl. .................................. 623/1; 623/12; 606/151
[58] Field of Search .................................. 623/1, 12, 11; 606/151

[56] References Cited

U.S. PATENT DOCUMENTS

| | | | |
|---|---|---|---|
| 5,697,971 | 12/1997 | Fischell et al. .............................. | 623/1 |
| 5,728,131 | 3/1998 | Frantzen et al. ......................... | 606/194 |
| 5,755,776 | 5/1998 | Al-Saadon .................................. | 623/1 |
| 5,776,183 | 7/1998 | Kanesaka et al. ........................... | 623/1 |

FOREIGN PATENT DOCUMENTS

| | | |
|---|---|---|
| 0 221 570 B1 | 1/1991 | European Pat. Off. . |
| 0 335 341 B1 | 3/1992 | European Pat. Off. . |

Primary Examiner—David H. Willse
Assistant Examiner—Suzette J. Jackson
Attorney, Agent, or Firm—Panitch Schwarze Jacobs & Nadel, P.C.

[57] ABSTRACT

A radially expandable support structure for holding open lumina within a body, especially in a blood vessel, has a tube-shaped body with a wall surface extending between a first and a second end which is formed from elongate members connected to each other. The elongate members include a first group of members which extend essentially in a longitudinal direction of the tube-shaped body, such that adjacent members of this first group are connected in pairs to each other at their ends to form a member pair which encloses a slit. These member pairs are connected approximately in the middle of their longitudinal extension to member pairs arranged adjacent to each other in a circumferential direction of the tube-shaped body to form a ring which surrounds the longitudinal axis of the tube-shaped body, and several rings connected to each other at the ends of the slits are arranged along the longitudinal axis of the tube-shaped body. In order to greatly decrease a reduction in length during the expansion of the support structure, the rings are connected to each other by a second group of elongate members, and each slit of a respective ring, as seen in the circumferential direction of the tube-shaped body, is arranged with a part of its length next to two respective slits of an adjacent ring, so that the slits of adjacent rings overlap.

13 Claims, 5 Drawing Sheets

RADIALLY EXPANDABLE SUPPORT DEVICE

CROSS-REFERENCE TO RELATED APPLICATIONS

This application is related to U.S. patent application Ser. Nos. 09/066,253 and 09/066,518, entitled "Radially Expandable Support Device II" and "Radially Expandable Support Device III," filed on Apr. 24, 1998 and assigned to the same assignee as the present invention and application.

BACKGROUND OF THE INVENTION

The invention involves a radially expandable support structure (e.g., a stent, graft or prosthesis) for holding open and/or expanding lumina within a body, especially in a blood vessel. The structure includes a tube-shaped body having a wall surface extending between a first and a second end which is formed from elongate members connected to each other, having a first group of members which extend essentially in the longitudinal direction of the tube-shaped body, wherein respectively adjacent members of this first group are connected in pairs to each other at their ends to form a member pair which encloses a slit or opening, wherein these member pairs are connected approximately in the middle of their longitudinal extension to member pairs arranged adjacent to each other in the circumferential direction of the tube-shaped body to form a ring around the longitudinal axis of the tube-shaped body, and wherein several rings connected to each other at the ends of the slits are arranged along the longitudinal axis of the tube-shaped body.

Support structures of this type are known, for example from European patent EP 335 341 B1. Support structures are described therein which are formed from elongate member pairs. These support structures are inserted into narrowed blood vessels or into other body passages having a lumen, in order to keep them open after expanding them by balloon dilatation. In this process, the support structures are expanded in their diameter and become shortened during expansion. This type of shortening is generally not desirable, however, since this shortening necessitates that a considerably longer support structure than is immediately required at the application site must be inserted into the body opening. The known structures adapt to the bends or curves in the body openings relatively poorly or not at all, so that additional bending components must be provided (EP 335 341 B1). The known support structures have rigid, tube-shaped sections which are connected flexibly to each other by hinged connections. In practice, it has generally been shown that tissue hypertrophy can occur in these hinged areas, caused by continuous agitation in the tissue seating area.

Other known structures exhibit pronounced shortening during expansion. Spiral structures are also known. These exhibit at their ends behavior unsuitable for insertion.

SUMMARY OF THE INVENTION

An object of the present invention is to create a radially expandable support structure which experiences none or only a very slight reduction in length during its expansion.

This object is achieved for the support structure described at the outset in that the rings are connected to each other by elongate members of a second group and that each slit of a respective ring is arranged having a part of its length next to two slits of a respectively adjacent ring, as seen in the circumferential direction of the tube-shaped body, so that the slits of adjacent rings overlap. A support structure of this type has almost no length reduction during expansion, since the elongate members of the second group in connection with the overlapping of the adjacent rings compensate for a length reduction of this sort. During the expansion of the support structure, the members of the first group, which originally extended in the longitudinal direction of the tube-shaped body, are deformed, for example kinked, at the connection points between member pairs adjacent to each other in the circumferential direction, so that the slits become expanded.

At the same time, the overlapping decreases so that the length reduction is compensated for. A support structure of this type is simultaneously constructed to be flexible. By the overlapping, a large number of slits is possible, as seen in the longitudinal direction, so that the individual members can be constructed very thin, without losing the effect of the lengthwise extension coupled to the expansion (by orienting the elongate members of the second group from the longitudinal direction the circumferential direction), which leads to the aforementioned lengthwise compensation.

It is expedient that each end of a slit is connected to the ends of both of the slits of an adjacent ring, which are adjacent due to the overlapping, in order to ensure a high degree of stability. For a high degree of flexibility, it is advantageous that each end of a slit is connected to the end of only one of the two slits of an adjacent ring, which are adjacent due to the overlapping. For this it can also be advantageous that not every slit is connected at its end with a slit of an adjacent ring.

In an advantageous embodiment, adjacent slits of a ring can be connected to each other by bridging links. The slits formed by the member pairs can have the shape of rhomboids or they can be constructed as ovals or rectangles. The slits can also be constructed as constant width openings from elongate members running parallel, wherein the ends are connected to each other in a rounded manner. By constructions of this type the bending behavior of the supporting structures can be influenced. Furthermore, the members of the first and second groups can have cross sections which differ from each other. Also in this manner, the bending capability of the structure is influenced. It is also possible that the cross section of one member changes along its length, for example diminishes from the middle to the ends. The expansion then occurs first at the ends of the member pairs; the corresponding material deformation in the middle area of the slits, where these are connected to the adjacent slits of a ring, follows thereafter. This has the consequence that all slits expand simultaneously under the action of force. It can also be expedient that the cross section of the elongate members of the first group is constructed square at their ends.

It can also be advantageous that the members of the second group connect the ends of the adjacent slits of adjacent rings together in a non-linear manner, i.e. for example in a curved manner. Furthermore, it is expedient to arrange at least four, and preferably six, slits adjacently next to each other in one ring around the circumference of the tube-shaped body.

As the material for the support structure, preferably one or more metals of the group tantalum, titanium, niobium, steel, platinum, or an alloy of at least one of these metals with at least one other metal (e.g., TaW, NbZr, TaNb, TiNb, TiAlV, PtIr, respectively in suitable weight proportions) can be used. This material can be coated with a biologically compatible material. The tube-shaped bodies are constructed from seamless tubes in order to avoid warping. The structures (the arrangement of the members) are manufactured by laser welding, electro-erosion, etching or by metal removal.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

Figure 1:
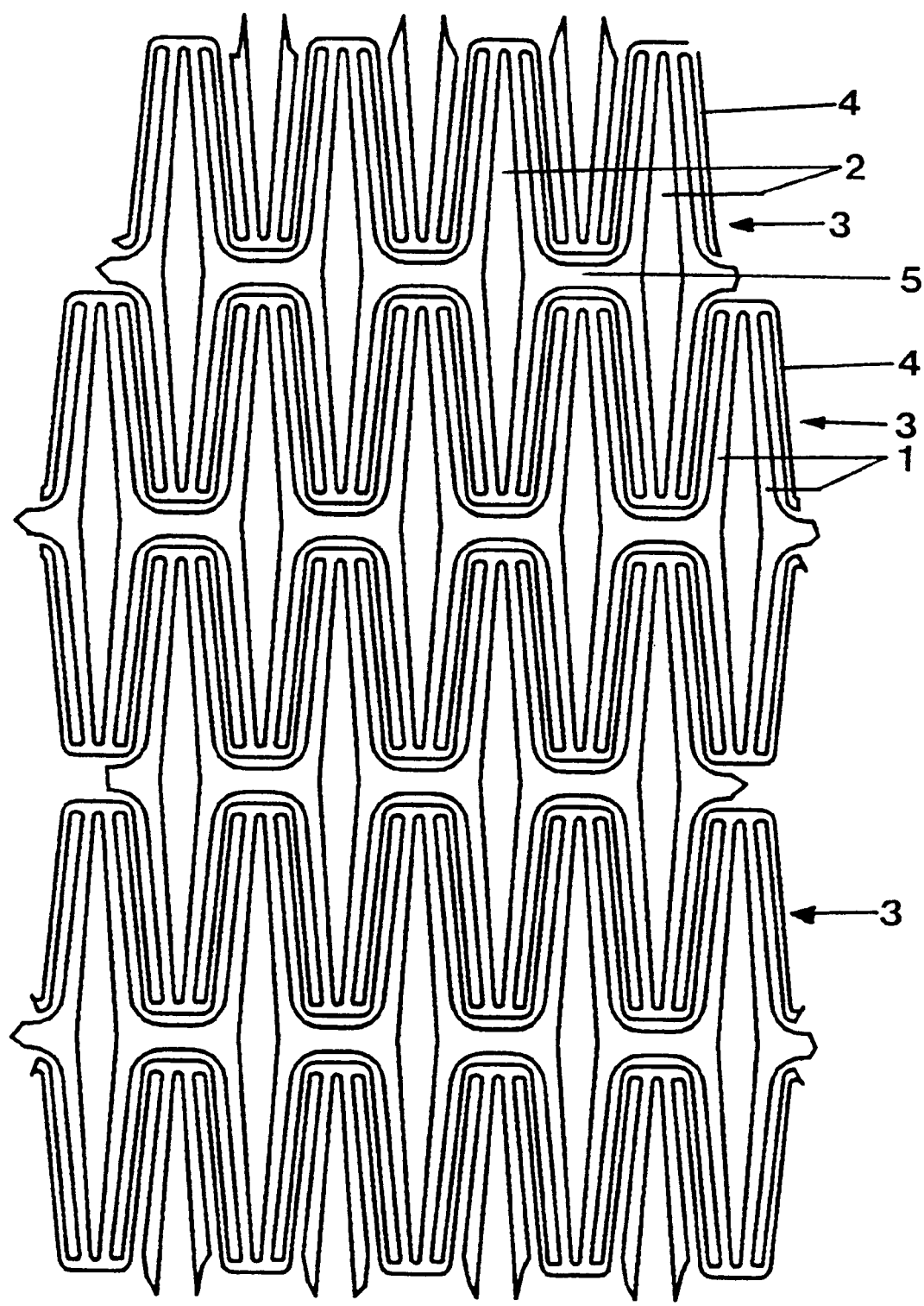
FIG. 1 shows a support structure in which each end of a slit is connected to each end of an adjacent slit.

The support structures shown in the drawings have slits constructed as rhomboids. Slits constructed in a different manner are sufficiently known from the prior art. For purposes of an overview, the drawings show a section of the supporting structure. The member pairs formed from members 1 of a first group, which respectively form a slit 2, are constructed in the longitudinal direction (vertical in the drawings) of the support structure and together form a tube-shaped body, as is sufficiently described in the prior art (e.g., EP 221 570 B1 or EP 335 341 B1). Thus, for overview purposes, only a section of the unrolled structure is depicted in the Figures.

Figure 2:
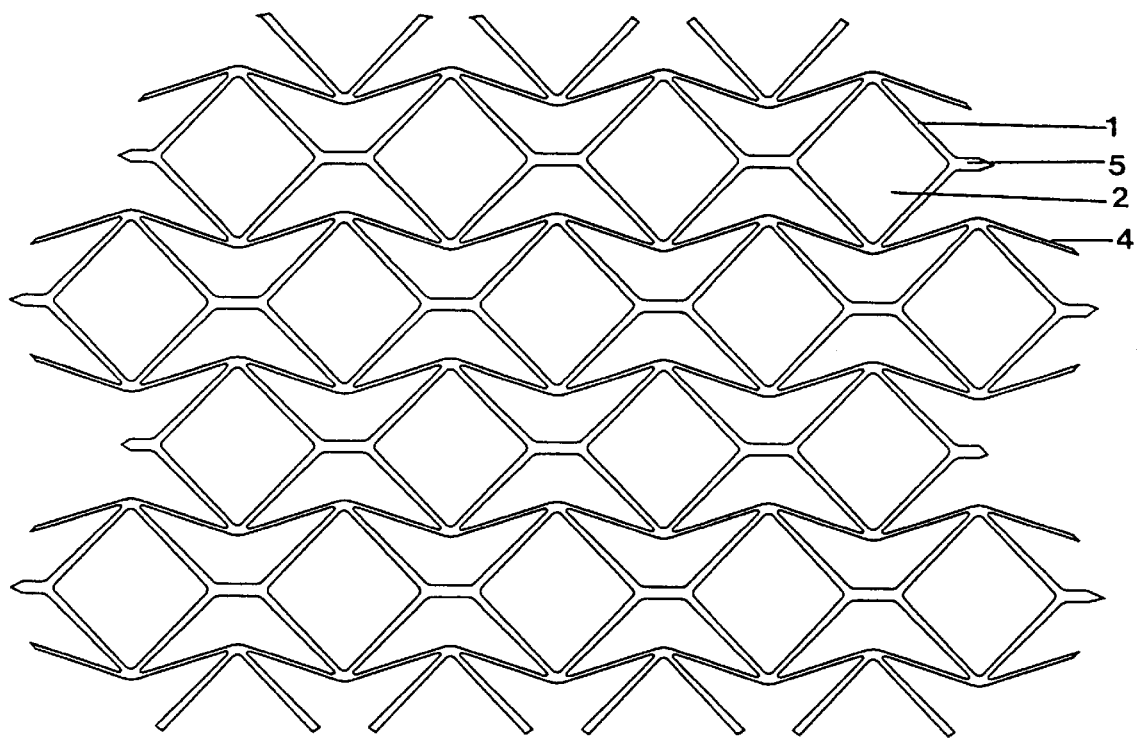
FIG. 2 shows the support structure of FIG. 1 in expanded condition.

In the support structure shown in FIG. 1, the slits formed by the members 1 in the circumferential direction with formation of a ring are connected to each other by bridging links 5 with adjacent slits 2. In the intermediate space formed by the bridging links 5, a respective end of a slit 2 of the adjacent ring 3 meshes. The ends of the slits 2 of adjacent rings 3, which are adjacent to each other in this manner, are respectively connected on both sides to members 4 of a second group, so that each slit 2 is connected at its ends to respective two slits 2 of adjacent rings 3. These members 4 of the second group are at first arranged approximately parallel to the members 1 of the first group. During expansion of the support structure these are oriented in the circumferential direction (horizontal in the drawings) of the support structure such that the ends of the slits 2 are set at a distance from the bridging links 5 of adjacent rings so that a longitudinal compensation of the support structure results (FIG. 2).

Figure 3:
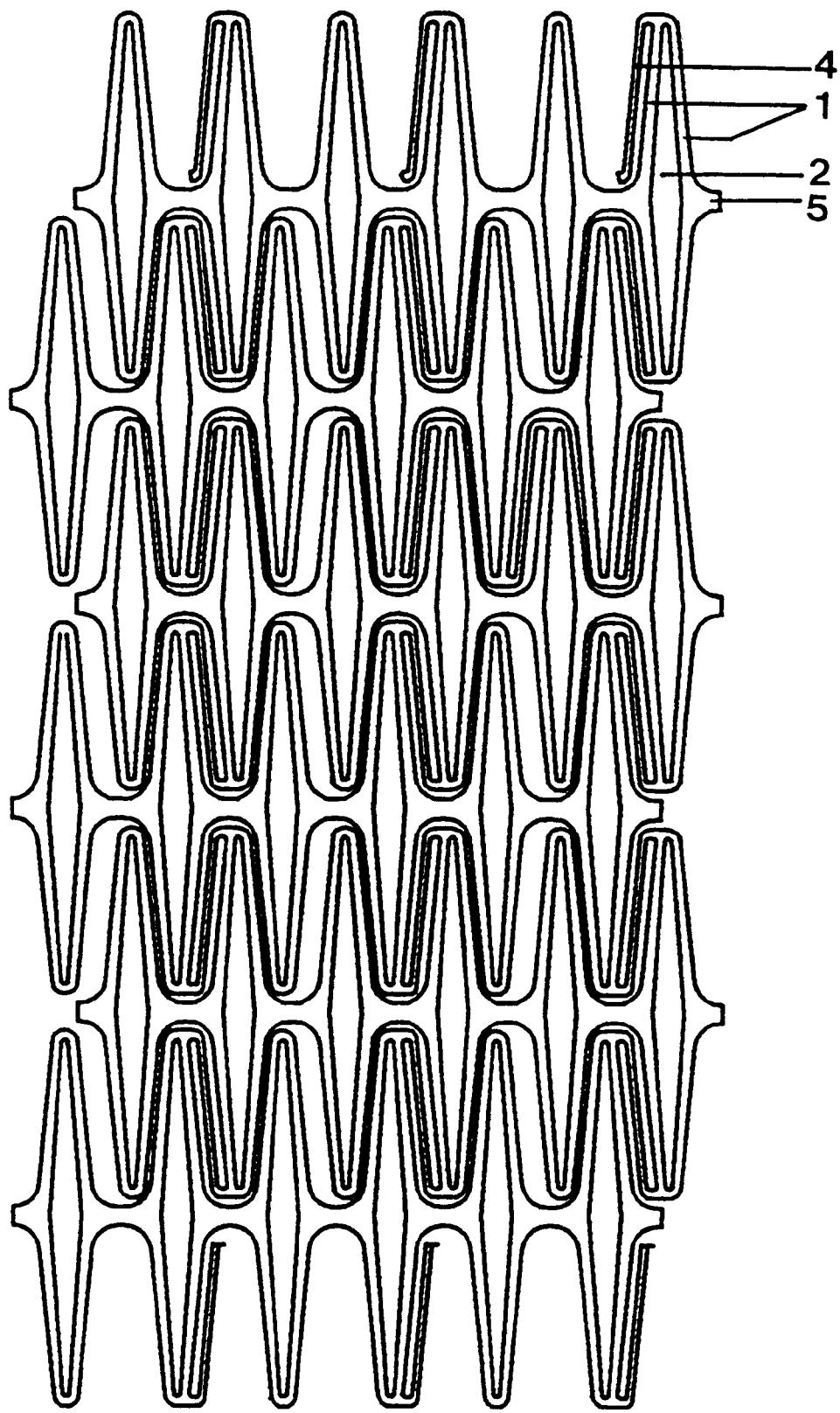
FIG. 3 shows a support structure in which some slits do not have any members of the second group on their ends.
Figure 4:
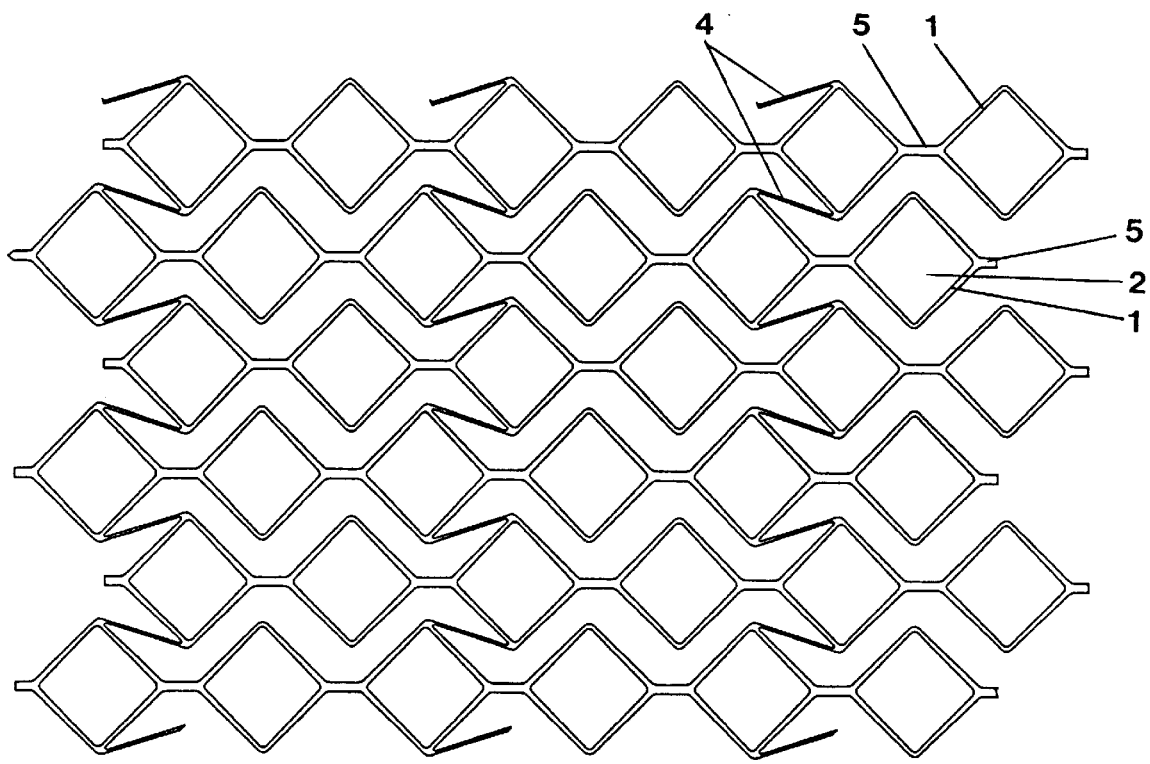
FIG. 4 shows the support structure according to FIG. 3 in expanded condition.

A similar support structure is shown in FIGS. 3 and 4. As opposed to the support structure shown in FIGS. 1 and 2, every second slit 2 of a ring 3 does not have any members 4 of the second group on the ends of the members 1 of the first group on the ends of the members 1 of the first group for connection to the ends of adjacent slits. A structure of this sort is more flexible than the support structure shown in FIGS. 1 and 2.

Figure 5:
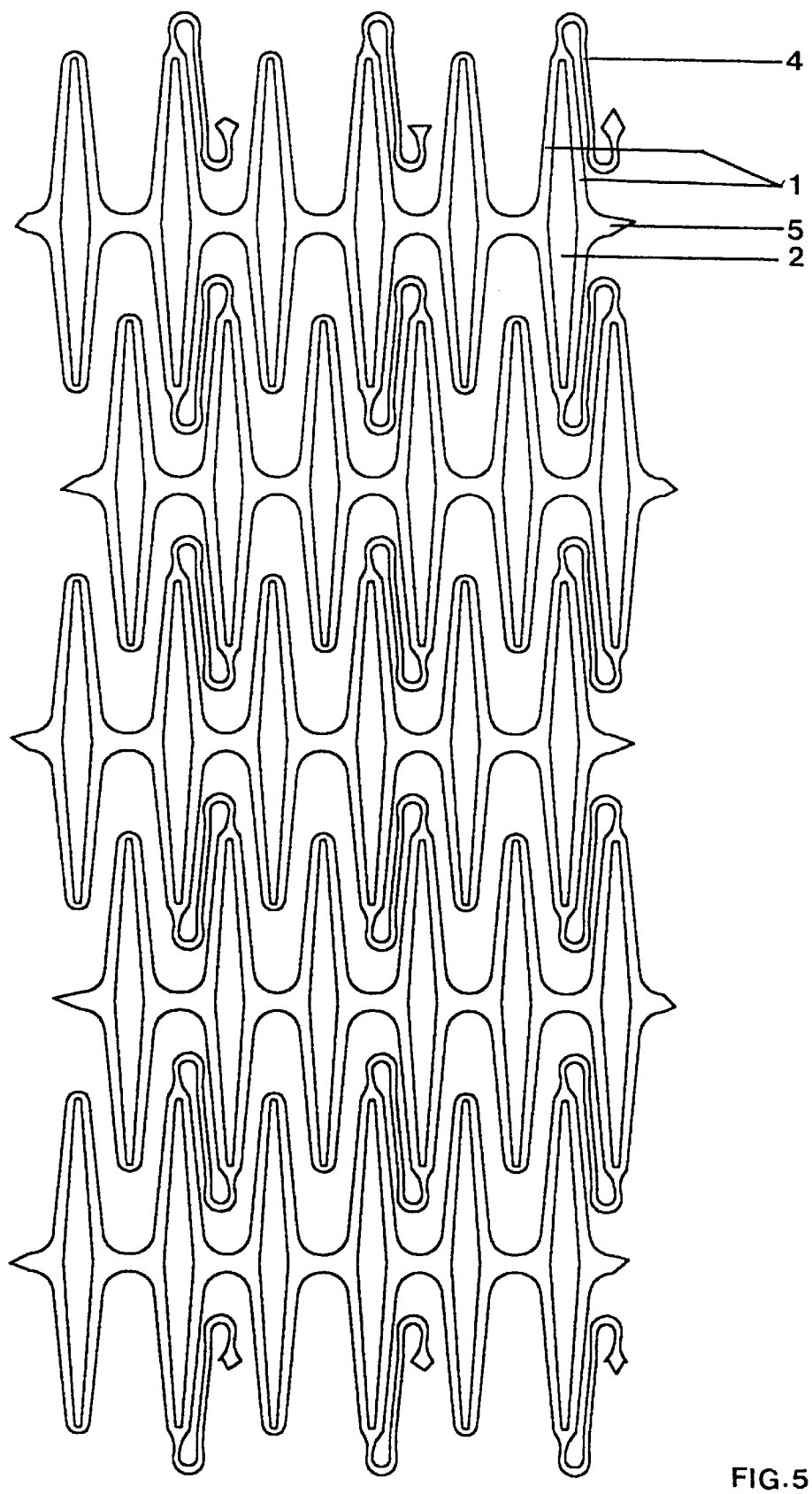
FIG. 5 shows a support structure according to FIG. 3 with curved members of the second group.

In FIG. 5 a support structure is depicted which is very similar to the one shown in FIG. 3, wherein the members 4 of the second group rest, in this example with a bend on the ends of the slits 2, so that a longer structure is present, as the linear connection between ends of adjacent slits 2 of overlapping rings 3, which results in an increase in flexibility. Here, also, as in the other examples, there are six slits 2 arranged on one ring 3. As a material, a medically suitable steel is used in the examples shown. This steel can be coated with a biologically compatible material, as is known for example from European patent EP 335 341 B1.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

I claim:

1. A radially expandable support structure for holding open a lumen within a body, particularly in a blood vessel, comprising:
    a tube-shaped body extending along a longitudinal axis, having a first end and a second end at opposite ends of the longitudinal axis, the body having a wall surface extending between the first and second ends, the wall surface further including:
        a plurality of first elongate members (1) which extend in a direction of the longitudinal axis and positioned circumferentially around the body, adjacent first elongate members having terminal ends that are connected to each other to form member pairs and the member pairs being connected approximately midway between the terminal ends of the first elongate members to adjacent member pairs to form a circumferential ring (3) disposed about the longitudinal axis of the body;
        each member pair encloses a slit (2) having terminal ends and a plurality of the circumferential rings (3) being arranged along the longitudinal axis of the body and being connected to one another in an area of the ends of the slits; and
        a plurality of second elongate members (4) connected between adjacent circumferential rings (3) of the body such that the terminal end of each slit (2) of one of the circumferential rings is disposed between the slits (2) of the adjacent circumferential ring (3) such that the slits (2) of adjacent circumferential rings (3) overlap.

2. The radially expandable support structure according to claim 1, wherein each end of a slit (2) is connected to ends of two adjacent slits (2) of an adjacent ring (3).

3. The radially expandable support structure according to claim 1, wherein each end of a slit (2) is connected to an end of only one of two adjacent slits (2) of an adjacent ring (3).

4. The radially expandable support structure according to claim 1, wherein not every slit (2) is connected at its ends to a slit (2) of an adjacent ring (3).

5. The radially expandable support structure according to claim 1, wherein adjacent slits (2) of a ring (3) are connected together by bridging links (5).

6. The radially expandable support structure according to claim 1, wherein the slits (2) have a shape selected from the group consisting of rhomboid, oval, and rectangle.

7. The radially expandable support structure according to claim 1, wherein the members (1) of the first group have cross sections different from the cross sections of members (4) of the second group.

8. The radially expandable support structure according to claim 1, wherein a cross section of the members (1, 4) changes over a length of the member (1, 4).

9. The radially expandable support structure according to claim 1, wherein the members (4) of the second group are constructed as a non-linear connection between two respective rings (3).

10. The radially expandable support structure according to claim 1, wherein at least four member pairs, each forming a slit (2), are arranged adjacent to each other around a circumference of the tube-shaped body.

11. The radially expandable support structure according to claim 1, wherein the structure is formed from a metal selected from the group consisting of tantalum, titanium, niobium, steel, platinum, and an alloy of at least one of these metals with at least one other metal.

12. The radially expandable support structure according to claim 1, wherein the structure is coated with a biologically compatible material.

13. The radially expandable support structure according to claim 1, wherein the slits (2) have a constant width opening and rounded connection points at their ends.

* * * * *